United States Patent
Saari et al.

(10) Patent No.: US 9,680,271 B2
(45) Date of Patent: Jun. 13, 2017

(54) SENSOR SYSTEMS AND METHODS FOR ANALYTE DETECTION

(71) Applicant: The Royal Institution for the Advancement of Learning / McGill University, Montreal (CA)

(72) Inventors: Jonathan Ikola Saari, Zurich (CH); Nate Quitoriano, Montreal (CA); James Forbes, Ypsilanti, MI (US); Gordon Roberts, Montreal-West (CA)

(73) Assignee: McGill University, Montreal (CA)

( * ) Notice: Subject to any disclaimer, the term of this patent is extended or adjusted under 35 U.S.C. 154(b) by 113 days.

(21) Appl. No.: 14/492,748

(22) Filed: Sep. 22, 2014

(65) Prior Publication Data

US 2016/0084705 A1 Mar. 24, 2016

(51) Int. Cl.
*G01N 33/00* (2006.01)
*H01R 43/00* (2006.01)

(52) U.S. Cl.
CPC ........... *H01R 43/00* (2013.01); *G01N 33/004* (2013.01)

(58) Field of Classification Search
None
See application file for complete search history.

(56) References Cited

U.S. PATENT DOCUMENTS

| | | | |
|---|---|---|---|
| 5,165,005 A | 11/1992 | Klainer et al. | |
| 7,257,279 B2 | 8/2007 | Guo et al. | |
| 7,510,882 B2 | 3/2009 | Vikholm et al. | |
| 7,697,796 B2 | 4/2010 | Kashyap et al. | |
| 8,195,014 B2 | 6/2012 | Heideman et al. | |
| 2011/0273709 A1 | 11/2011 | Sweeney | |
| 2012/0170044 A1* | 7/2012 | Prabhakar | G01N 21/05 356/440 |
| 2013/0146865 A1 | 6/2013 | Jang et al. | |
| 2014/0200054 A1 | 7/2014 | Fraden | |

FOREIGN PATENT DOCUMENTS

WO WO-2014/066826 5/2014

OTHER PUBLICATIONS

Coss, P.M. et al. Microwave Regeneration of Activated Carbon Used for Removal of Solvents from Vented Air, 2000, J. Air & Waste Manage. Assoc. vol. 50, pp. 529-535.*
International Search Report and Written Opinion in International Application No. PCT/IB2015/057305, mailed Dec. 24, 2015 (12 pages).

(Continued)

*Primary Examiner* — Robert Xu
(74) *Attorney, Agent, or Firm* — Maschoff Brennan

(57) ABSTRACT

Systems for analyte detection are disclosed. The system includes absorption channels positioned along a surface of an object. The absorption channels are configured to trap an analyte. The system further includes a sensor embedded in the object and configured to detect the presence of the analyte. The sensor includes a light source configured to transmit light and a detector configured to detect a change in an intensity of light transmitted by the light source. The sensor further includes a cable configured to connect the light source to the detector, wherein the cable comprises detection regions, and wherein the detection regions include a portion of the cable exposed to the analyte in the absorption channel.

20 Claims, 9 Drawing Sheets

(56) References Cited

OTHER PUBLICATIONS

"UC Research on Embedded Sensors for Tracking Gas Leaks," published on May 17, 2010, Accessed at http://www.azosensors.com/News.aspx?newsID=433, Accessed on Jul. 16, 2014, pp. 2.

Axelrod, D. et al., "Total internal reflection fluorescent microscopy," Journal of Microscopy, vol. 129, No. 1, pp. 19-28 (1983).

Buric, M. P. et al., "Optical fiber evanescent absorption sensors for high-temperature gas sensing in advanced coal-fired power plants," Proc. SPIE 8463, Nanoengineering: Fabrication, Properties, Optics, and Devices IX, 84630D, pp. 14 (2012).

Cao, Y. C. et al., "Gas detection with evanescent-wave quartz-enhanced photoacoustic spectroscopy," Proc. SPIE 8351, Third Asia Pacific Optical Sensors Conference, pp. 835121, (2012).

Díaz, E. et al., "Comparative study on the gas-phase adsorption of hexane over zeolites by calorimetry and inverse gas chromatography," Journal of Chromatography A, vol. 1095, pp. 131-137 (2005).

Foster, K. L. et al., "Adsorption Characteristics of Trace Volatile Organic-Compounds in Gas Streams Onto Activated Carbon010Fibers," Chem. Mat., vol. 4, No. 5, pp. 1068-1073 (1992).

Gilbert, S.L., "Carbon Monoxide Absorption References for 1560nm to 1630nm Wavelength Calibration," National Institute of Standards and Technology, 260-146, pp. 37 (2002).

McDonagh, C. et al., "Tailoring of so-gel films for optical sensing of oxygen in gas and aqueous phase," Anal. Chem., vol. 70, No. 1, pp. 45-50 (1998).

Pickrell, G. et al., "Random-hole optical fiber evanescent-wave gas sensing," Opt. Lett., vol. 29, pp. 1476-1478 (2004).

Tai, H. et al., "Fiber-optic evanescent-wave methane-gas sensor using optical absorption for the 3.392-μm line of a He-Ne laser," Opt. Lett., vol. 12, No. 6, pp. 437-439 (1987).

Yan, G. F. et al., "Fiber-Optic Acetylene Gas Sensor Based on Microstructured Optical Fiber Bragg Gratings," IEEE Photonics Technol. Lett., vol. 23, No. 21, pp. 1588-1590 (2011).

\* cited by examiner

SENSOR SYSTEMS AND METHODS FOR ANALYTE DETECTION

BACKGROUND

The following description is provided to assist the understanding of the reader. None of the information provided or references cited is admitted to be prior art.

Sensors can be used to detect various characteristics of an environment surrounding the sensor. For example, a chemical sensor can provide information related to the chemical composition of the environment surrounding an individual. The technology can have broad applications including environmental chemical monitoring, workplace safety monitoring, industrial process control, quality control, leak testing, biomedical monitoring, food and water testing, and drug detection.

SUMMARY

The present technology provides a system for detecting analytes. The system includes absorption channels positioned along a surface of an object. The absorption channels can be configured to trap an analyte. The system further includes a sensor embedded in the object and configured to detect the presence of the analyte. The system includes a light source configured to transmit light and a detector configured to detect a change in an intensity of light transmitted by the light source. The system further includes a cable configured to connect the light source to the detector. The cable can include detection regions. The detection regions can include a portion of the cable exposed to the analyte in the absorption channel.

The present technology further provides a method for detecting analytes. The method includes transmitting, by a light source, light through a cable and propagating, by the cable, the light via internal reflection as the light is transmitted through the cable. The method further includes emitting, by detection regions of the cable, an evanescent wave into absorption channels in response to the internal reflection. The method further includes detecting, by a detector, a change in an intensity of light transmitted through the cable. The change in the intensity of light transmitted through the cable indicates the presence of an analyte in the absorption channels.

The present technology further provides a method for creating an analyte detection system. The method includes forming absorption channels along a surface of an object. The absorption channels can be configured to trap an analyte. The method further includes embedding a sensor in the object. The sensor can be configured to detect the presence of the analyte. The sensor includes a light source configured to transmit light and a detector configured to detect a change in an intensity of light transmitted by the light source. The method further includes connecting the light source to the detector via a cable. The cable can include detection regions. The detection regions can include a portion of the cable exposed to the analyte in the absorption channel.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

DETAILED DESCRIPTION

Figure 1:
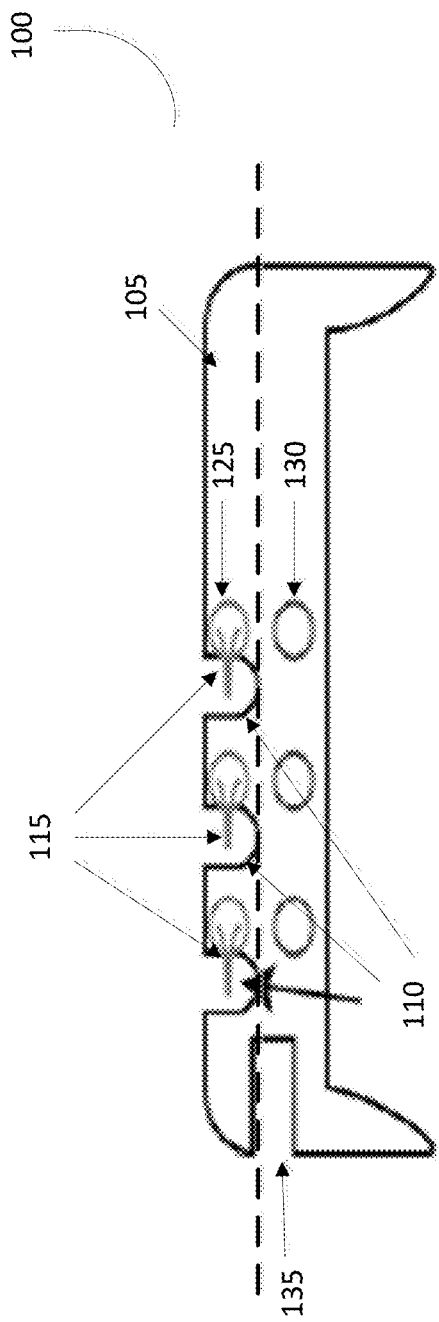
FIG. 1 depicts an illustration of a sensor system for detecting analytes in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The present technology is directed to systems and methods for analyte detection. An analyte is a chemical or gas substance subject to chemical analysis. To detect the presence of analytes, a chemical sensor system can be created that is adaptable to mobile devices. The technology has broad application including environmental chemical monitoring, workplace safety monitoring, industrial process control, quality control, leak testing, biomedical monitoring, food and water testing, and drug detection.

In an embodiment, the chemical sensor can be embedded into a mobile device, for example, a mobile phone case. When embedding the chemical sensor in the mobile phone case, the chemical sensor has a simple design and reduced manufacturing costs since the mobile phone case does not contain other electronics or components. Therefore, the chemical sensor does not have to be designed around additional components as it would if it was embedded in an existing electronic device. Additionally, the mobile phone case provides more space for optical fibers to be used in detecting various analytes than if the chemical sensor was embedded in another device. In an embodiment, the chemical sensor enables an individual user to verify that food or drink is safe to consume. Additionally, still in another embodiment, the chemical sensor can be used to detect various allergens in the environment around the individual. The environment can vary. For example, the environment may include the individual's home, an outdoor park, an office building, or any other suitable environment.

The minimal size of the chemical sensor according to the embodiments discussed below allows for use of the chemical sensor in many different applications without adapting or altering the chemical sensor. The chemical sensor makes use of evanescent wave absorption spectroscopy to detect the presence of analytes in the environment around a user of the mobile device. In addition, the chemical sensor can generate alerts to notify the individual of the presence of dangerous gases.

FIG. 1 depicts an illustration of a sensor system 100 for detecting analytes in accordance with an illustrative embodiment. The sensor system 100 includes absorption channels 110 and a sensor 115. In an embodiment, the absorption channels 110 are positioned along a surface of an object 105. The sensor 115 is embedded in the object 105. In an embodiment, the object 105 is made of a polymer matrix material. In other embodiments, the object 105 may be made up of titanium or activated carbon.

The object 105 can be adaptable for a mobile device or a computing device, for example, a hand-held computing device. In one embodiment, the object 105 is a mobile phone case. In other embodiments, the object 105 is a mobile phone. In an embodiment, the length of the absorption channels 110 is about equal to the length or width of the object 105. For example, the absorption channels 110 may run along the entire length of a face of a mobile phone case. In an embodiment, the width of the absorption channels may be about 1 millimeter (mm). The depth of the absorption channels 110 may be about 1 mm deep. In other embodiments, the dimensions of the absorption channels 110 may be any length, width, and/or depth that is suitable for a design need of the device.

The object 105 includes an exposed layer 125 and a protected layer 130. The exposed layer 125 is exposed to an environment within the absorption channels 110. Each absorption channel 110 may include, for example, a hole formed into the surface of the absorption channel 110. The hole exposes the sensor 115 to elements, chemicals, and/or gases present in the absorption channels 110 and leaves the sensor 115 unprotected. The hole may run the entire length of the corresponding absorption channel 110. In an embodiment, the absorption channels 110 may include any type of hole or slit of any length and/or diameter that is suitable for a design need of the device to expose the sensor 115 to the environment around the object 105.

In some embodiments, an absorption channel 110 can be covered in an index matching material. The index matching material can be a liquid, adhesive, or a gel. In an embodiment, the index of refraction of the index matching material matches the index of refracting of a cladding layer of a cable in the sensor 115. The index of refraction of the index matching material may be greater than the index of refraction of the air in the environment around the object 105.

In some embodiments, each absorption channel 110 has the same size exposed layer 125. In other embodiments, the size of the exposed layer 125 may vary between each of the absorption channels in the sensor system 100. The exposed layer 125 allows the sensor 115 to interact with the elements present in the absorption channel 110. The absorption channels 110 will be discussed in greater detail below with respect to FIG. 4.

As mentioned above, the object 105 includes protected layer 130. The protected layer 130 is isolated from the environment of the absorption channels 110. In some embodiments, the protected layer 130 may be located entirely inside the object 105. Indeed, according to various embodiments, the protected layer 130 is protected from and therefore unaffected by elements present in the absorption channels.

The sensor 115 includes a cable. In an embodiment, the cable is an optical fiber. In some embodiments, the cable is an optical waive guide with a blazed fiber Bragg grating (FBG). The thickness of the cable can range from about a few microns to about a few hundred microns. In one embodiment, the thickness of the cable is about 125 microns. The cable traverses the inside of the object 105 through the exposed layer 125 and/or the protected layer 130. In some embodiments, the cable that passes through the protected layer 130 may be referred to as a reference cable. The sensor 115 and the cable will be discussed in greater detail below with respect to FIG. 2.

The sensor system 100 also includes a universal serial bus (USB) port 135. The sensor 115 can connect directly to a mobile device via the USB port 135. The sensor 115 communicates and transmits data to the mobile device through the USB port 135. The sensor 115 can be powered by the mobile device through the connection established by the USB port 135. For example, the sensor 115 functions with any device capable of powered USB interfacing through the USB port 135. Example devices may include at least one of a laptop, cell phone, tablet computer, or any type of handheld computing device. In other embodiments, the sensor system 100 is battery powered. In alternative embodiments, the USB port 135 may be omitted from the sensor system 100, and alternative communication methods as known to those of skill in the art may be used to convey data from the sensor system 100 to external devices.

Figure 2:
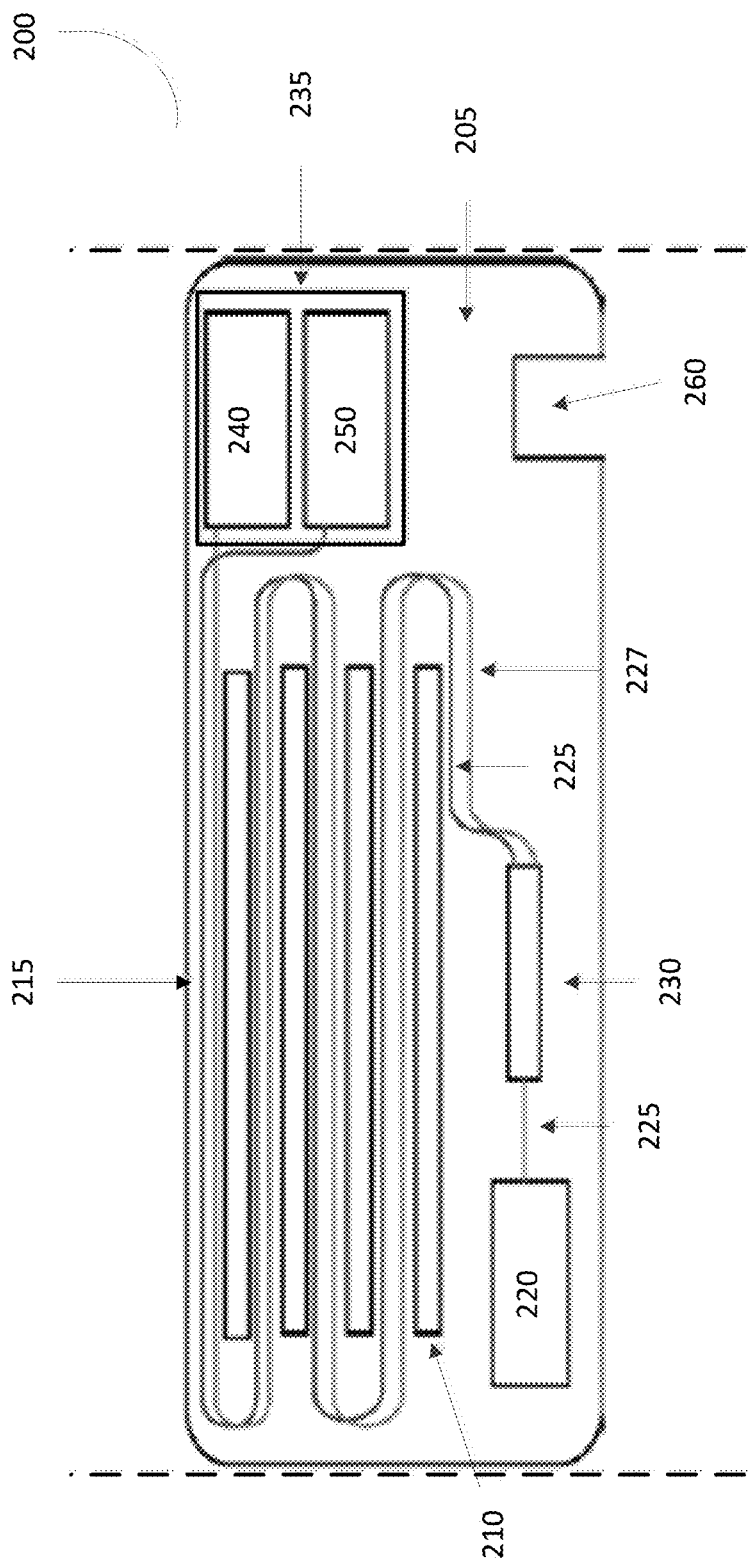
FIG. 2 depicts a cut-away view of a sensor system for detecting analytes in accordance with an illustrative embodiment.

FIG. 2 depicts a cut-away view of a sensor system 200 for detecting analytes in accordance with an illustrative embodiment. In particular, FIG. 2 depicts the sensor system 100 from FIG. 1, exposed along the dashed line to reveal the interior of the sensor system 100. The sensor system 200 includes absorption channels 210 and a sensor 215. The absorption channels 210 are formed in an object 205, and the sensor 215 is embedded in the object 205. In an embodiment, the sensor 215 is a chemical sensor embedded in the object 205. The sensor 215 includes a light source 220, a detector 235, and a cable 225 configured to connect the light source 220 to the detector 235.

In one embodiment, the light source 220 is an infrared (IR) light-emitting diode (LED). In another embodiment, the light source 220 is a light source from a mobile phone. The light source 220 is configured to transmit light through the cable 225 to the detector 235. In some embodiments, the sensor includes an optical coupler 230 disposed between the light source 220 and the detector 235. The optical coupler 230 can be connected to one or more input cables and one or more output cables. The optical coupler 230 combines or splits received light. For example, the optical coupler 230 receives light from the one or more input cables and transmits light to the one or more output cables. In one embodiment, the optical coupler 230 includes a 1:2 optical coupler and is configured to transmit light from the light source 220 to the cable 225 and a reference cable 227. The 1:2 optical coupler receives light from the light source 220 via the cable 225 and then splits the light such that it is transmitted to the detector 235 via both the cable 225 and the reference cable 227.

The cable 225 traverses the inside of the object 205 to connect the light source 220 to the detector 235. The cable 225 can include detection regions. The detection regions include a portion of the cable 225 that is exposed to the external environment of the sensor system 200 within the absorption channels 210. In this way, the detection regions may be exposed to analytes within the absorption channels 210. In some embodiments, the detection regions align with the exposed layer of the object 205, as described above with respect to FIG. 1. The absorption channels 210 can include a hole formed into the channel and the detection regions can be aligned with these holes in the absorption channels 210 to be directly exposed to the environment in the absorption channels 210. The dimensions of the detection regions can be about equal to the length of the object 205 and/or the length of the corresponding absorption channel 210. In one embodiment, the length of the detection region is equal to the length of the corresponding absorption channel 110.

In an embodiment, the detection regions of the cable 225 are configured to emit an evanescent wave into the absorption channels. In an embodiment, each of the detection regions is exposed in a different absorption channel 210. Each of the absorption channels 210 can include a hole formed into it to expose the detection region to the environment in the absorption channel 210.

The reference cable 227 connects the light source 220 to the detector 235 and is protected from the absorption channels 210. The reference cable 227 traverses the inside of the object 220 to connect the light source 205 to the detector 235; however, the reference cable is isolated from the absorption channels 210. In an embodiment, the reference cable 227 traverses the inside of the object 205 through a protected layer of the object 205. In some embodiments, the reference cable 227 is not exposed to the environment of the absorption channels 210 and does not include detection regions. The reference cable 227 follows a similar path as the cable 225 inside the object 205, but the reference cable 227 is optically isolated from the absorption channels 210. The light transmitted by the reference cable 227 is measured and/or compared to the light transmitted by the cable 225 to detect a change in intensity of light transmitted by the cable 225. In an embodiment, the reference cable 227 and the cable 225 each include a same cable-type and/or material. In other embodiments, the reference cable 227 is a different cable-type and/or material than the cable 225.

The detector 235 is configured to detect a change in an intensity of light transmitted by the light source 220. In one embodiment, the detector 235 is a photodetector (for example, a photodiode) configured to measure an amount of light transmitted by the light source 220 via the cable 225 and/or the reference cable 227. In other embodiments, the detector 235 is a charged couple device (CCD) camera. The detector 235 can be configured to convert light into either a current or a voltage reading. The detector 235 transmits a measured light intensity from the cable 225 and/or the reference cable 227 to a processor. As discussed in more detail below, the processor is configured to analyze the measured light intensity and make determinations about analytes within the environment of the sensor system 200 based on the measured light intensity.

In an embodiment, the detector 235 includes multiple detection diodes. Each detection diode can be connected to a different cable in the sensor system 200. In one embodiment, the detector 235 includes a signal detector 240 and a reference detector 250. The signal detector 240 can be connected to the cable 225 and is configured to receive light from the light source 220 via the cable 225. The reference detector 250 can be connected to the reference cable 227 and is configured to receive light from the light source 220 via the reference cable 227.

The sensor system 200 includes a universal serial bus (USB) port 260. The sensor 215 can be similar to the USB port 135 described above with respect to FIG. 1. The sensor 215 connects directly to a mobile device via the USB port 260. The sensor 215 communicates and transmits data to the mobile device through the USB port 260. In an embodiment, the sensor 215 is powered by the mobile device through the connection established by the USB port 260. For example, the sensor 215 can function with any device capable of powered USB interfacing through the USB port 260. Example devices include at least one of a laptop, cell phone, tablet computer, or any type of handheld computing device. In other embodiments, the sensor system 200 is battery powered and the USB port 260 may be omitted.

The sensor system 200 can include a processor. In an embodiment, the processor is a microprocessor of a mobile device. In some embodiments, the processor is coupled to the sensor 215. In one embodiment, the processor is communicatively coupled to the sensor 215. The processor can be configured to receive data from the sensor 215. The data may include the intensity of light transmitted through the cable 225 and/or the reference cable 227 detected by the sensor 215.

The processor is configured to compare the intensity of light transmitted through the cable 225 and/or the reference cable 227 detected by the embedded sensor to a calibration curve. The calibration curve may include threshold value(s) for an environment of clean air. In some embodiments, a calibration curve is used to determine the presence of an analyte. The calibration curve determines the presence of the analyte and the concentration of the analyte by comparing the calibration curve to measured data. The calibration curve may include a set of standard samples of known concentrations of a target analyte. The calibration curve will be described in greater detail with respect to FIG. 6.

The processor can be configured to generate a notification to a user in response to the comparison of the intensity of light transmitted through the cable 225 and/or the reference cable 227 detected by the sensor 215 to the calibration curve. The notification may indicate a presence of an analyte. The notification can include at least one of an auditory, a visual, a tactile, or any other suitable notification. In an embodiment, the notification includes instructing and/or operating components of a mobile device to generate the notification. The auditory notification can include generating a noise or sound to notify a user of the mobile device to the presence of the analyte. For example, the auditory notification can include an alarm ringtone. The visual notification can include generating a visual alert to notify the user of the mobile device of the presence of the analyte. The visual alert can include a flashing LED and/or a flashing symbol on a user interface screen of the mobile device. The tactile notification can include generating a tactile alert to notify the user of the mobile device of the presence of the analyte. In an embodiment, the tactile notification includes a vibrating sensation, for example, vibrating the mobile device to alert the user. In some embodiments, a combination of auditory, visual, and tactile alerts are used to notify the user of the mobile device.

As illustrated in FIG. 2, the cable 225 and reference cable 227 traverse the inside of the object 205 to connect the light source 220 to the detector 235. In some embodiments, light transmitted by the light source 220 can propagate through the cable 225 and the reference cable 227 by total internal reflection fluorescence (TIRF), for example, as illustrated in FIG. 3.

Figure 3:
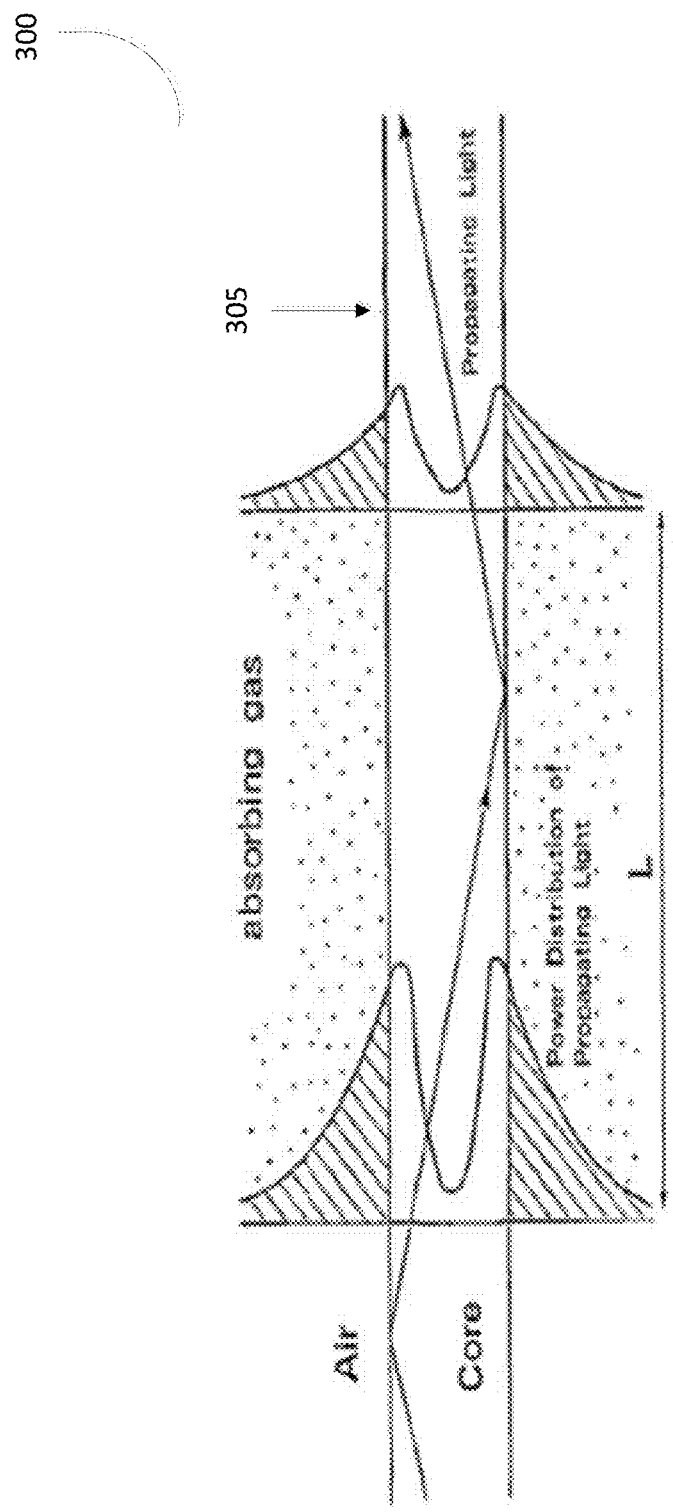
FIG. 3 depicts an illustration of an intensity profile of propagating light through an optical fiber in accordance with an illustrative embodiment.

FIG. 3 depicts an illustration of an intensity profile of propagating light through a cable 305 (for example, an optical fiber) in accordance with an illustrative embodiment. TIRF occurs when incident light approaches an interface consisting of two different indices, for example, $n_1$ and $n_2$, at an angle greater than the critical angle, $\theta_c$, which can be described by the following equation:

$$\theta_c = \arcsin\left(\frac{n_1}{n_2}\right)$$

In an embodiment, the cable 305 is configured to emit an evanescent wave in response to TIRF. Following TIRF, an exponentially decaying electromagnetic field, or evanescent wave, is emitted from the core of the cable 305. This evanescent wave can be used to, for example, excite a fluorophore or biological tag in TIRF microscopy. In some embodiments, the evanescent wave is used in an absorption scheme, for example, evanescent wave absorption spectroscopy.

In the presence of an analyte, the evanescent wave will be absorbed by the analyte in at least one of the absorption channels of a sensor system. The detection region of the cable 305, length 'L' in FIG. 3, is exposed to an environment in an absorption channel. The propagating optical wave produces an evanescent wave with a power profile outside a waveguide as represented in FIG. 3 by the striped lines. As the evanescent wave propagates through the air, the wave is absorbed by an analyte (represented by dots in FIG. 3) that is present in the environment of the absorption channel. This absorption of the evanescent wave leads to a reduction of the overall intensity of the evanescent wave as it is transmitted to a detector. The absorption is detected by measuring the reduction in the intensity of the propagated light through the cable 305. The reduction can be measured by a detector of the sensor system as discussed above with respect to FIG. 2. The transmittance of the cable 305 is denoted by the symbol P and is given by the following equation:

$$P = P_o e^{-\alpha r \mu L}$$

Where $P_o$ is the transmittance in the absence of the absorbing gas, $\alpha$ is the absorption coefficient of the gas in free space, r is the ratio of intensity of the evanescent wave to that of the propagating wave, L is the length of the exposed portion of the cable 305, and $\mu$ is the gas coefficient. It can be seen that the sensitivity of the detector will increase with the length of the exposed cable 305. In some embodiments, for example, when the sensor system is embedded into a mobile phone case, the large surface area of the mobile phone case provides a suitable medium for supporting cable bundles for this task.

Figure 4:
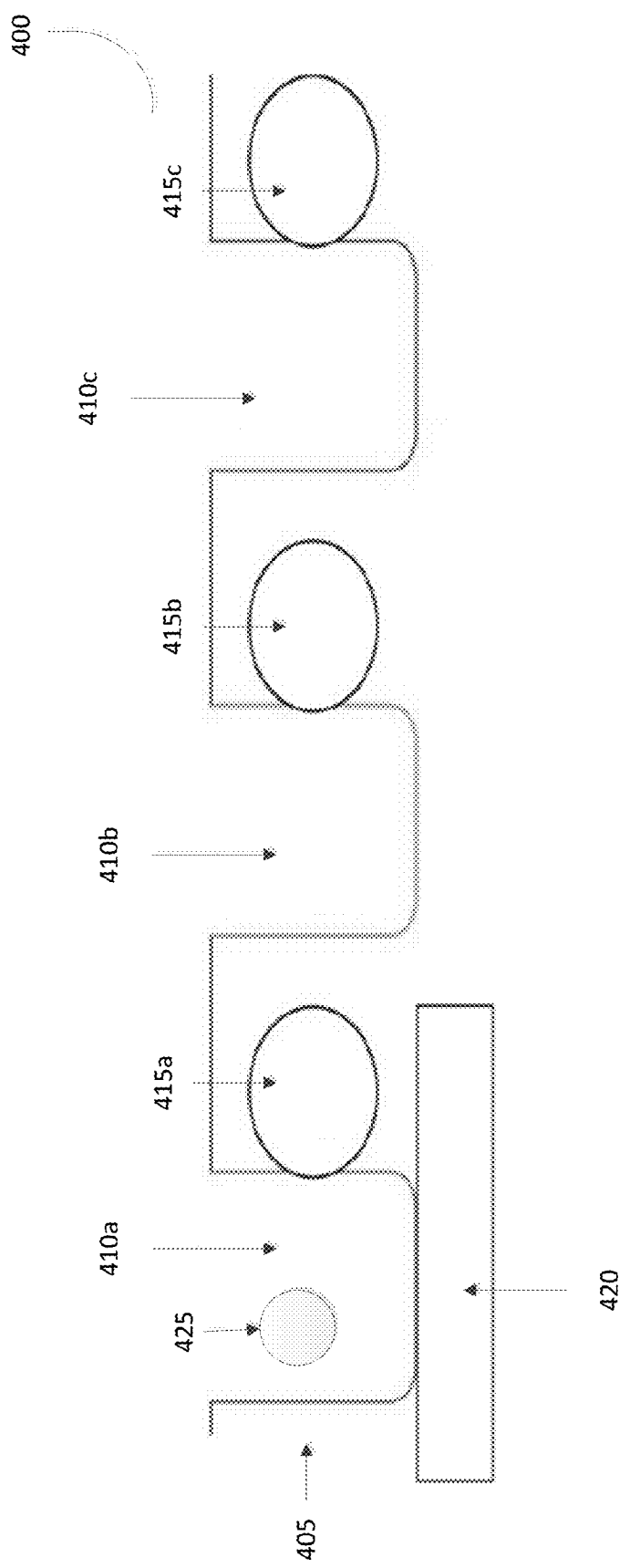
FIG. 4 depicts an illustration of a perspective view of a sensor system for detecting analytes in accordance with an illustrative embodiment.

FIG. 4 depicts an illustration of a perspective view of a sensor system 400 for detecting analytes in accordance with an illustrative embodiment. The sensor system 400 includes portions of a cable 415a-c exposed to an environment in absorption channels 410a-c. In an embodiment, the absorption channels 410a-c are formed into a surface of an object 405.

In some embodiments, the absorption channels 410a-c are grooves formed into a surface of the object 405. The shape of the absorption channels 410a-c can vary in accordance with different embodiments. For example, the shape may include one of an arc, a semicircle, or a half of a square. In an embodiment, the absorption channels 410a-c can all be the same shape. In other embodiments, the shape of the absorption channels 410a-c varies from one channel to the next channel within a single sensor system 400.

As illustrated in FIG. 4, an analyte 425 is present in the environment of the absorption channel 410a. To detect the analyte 425, the absorption channels 410 a-c are chemically coated with a material 420. The chemical coating creates a chemoselective environment within the absorption channels 410a-c. The chemoselective environment can selectively react with one functional group as opposed to another thereby allowing the absorption channels 410a-c to trap the analyte 425 (which is configured to selectively react with the one functional group). The analyte 425 can be any type of volatile organic compound (VOC). For example, the analyte 425 may include at least one of carbon monoxide, acetone, cyclohexane, hydrogen gas, carbon dioxide, nitrogen, or ammonia. In an embodiment, the analyte 425 may be any type of gaseous compound including an oxygen molecule or nitrogen molecule.

In some embodiments, the absorption channels 410a-c are chemically coated with a material 420 that is configured to attract a target analyte 425. The material 420 can be selected to promote at least one of physisorption or chemisorption within the absorption channels 410a-c when the analyte 425 is present within the environment of the sensor system 400. The surface of the absorption channels 410a-c are chemically coated with the material 420 dependent on the VOC to be detected. In various embodiments, the material 420 can include at least one of sulfur, aluminum-doped graphene, activated carbon, or a zeolite mineral. In additional embodiments, the material 420 can also include at least one of various organic semiconductor inks, dielectric inks, or metallic inks.

In an embodiment, the chemically-coated absorption channels 410a-c absorb specific types of analytes either through physisorption or chemisorption. Physisorption is the near-field interaction between a surface (for example, the surface of the absorption channels 110) and a gas (for example, an analyte). It is a phenomenon reliant on van der Wall forces. In essence, as a gas approaches a given solid surface (for example, the chemically-coated absorption channel), the physisorption potential, V, increases with a $Z^3$ dependence, where Z is the distance between the gas and the surface.

Chemisorption is a specific case of physisorption wherein the attraction is stronger than just van der Walls forces. Indeed, the enthalpy for absorption in the case of physisorption is roughly −30 kilojoules/mole (kJ/mol), whereas that for chemisorption is in the −100 kJ/mol range. Generally, the gas interacts with the surface through the direct donation of electron density, sometimes resulting in a covalent bond. The chemisorbed gas storm or molecule likely resided first in a physisorbed precursor state. The residence time for a physisorbed atom or molecule at room temperature is short, on the order of a few hundred picoseconds. However, the residence time for chemisorption is on the order of minutes to hours. It is the residence time that allows one to develop chemo-selectivity in gas-phase chemisorption spectroscopy experiments, and similarly, in the sensor systems as described herein.

To detect different and/or multiple types of VOC's, for example, analyte 425, the absorption channels 110 can be chemically coated with different types of materials 420. In some embodiments, all of the absorption channels 410a-c are chemically coated with the same material 420. In other embodiments, each of the absorption channels 410a-c is chemically coated with a different material 420.

The cable 415 may include a portion directly exposed to the absorption channel 410a-c. It is through this direct contact that the evanescent wave absorption spectroscopy can be performed. Light propagated through the cable 415, in the presence of the analyte 425, is absorbed. This absorption results in a lower intensity of light transmitted through the cable 415 and is detected by a detector. The absorption leads to a reduced voltage reading interpreted by the detector and/or a processor, for example, a microprocessor of a mobile device. This reduction in voltage can be reported to an end user to notify the user of the presence of the analyte 425 in a surrounding environment that the sensor system 400 is present in.

In order to account for fluctuations in the source intensity, a reference cable, for example, reference cable 227 described above with respect to FIG. 2, can be included in the sensor system 400. The reference cable follows the same or similar path as the cable 415; however, the reference cable will be isolated from the environment of the absorbing channels 410a-c. The measured intensity of light propagated through cable 415 is compared to the measured intensity of light propagated through the reference cable, as illustrated in FIGS. 5A and 5B.

Figure 5A:
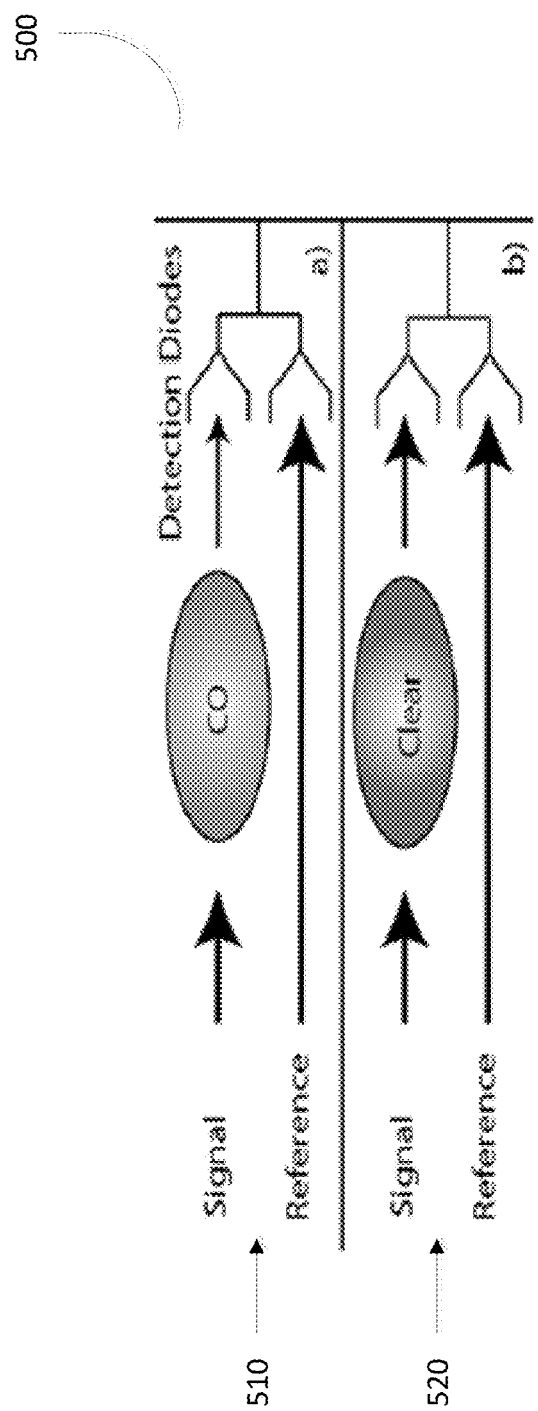
FIG. 5A depicts an illustration of a comparison of detection diodes in accordance with an illustrative embodiment.

FIG. 5A depicts an illustration of two comparisons 500 of detection diodes in accordance with an illustrative embodiment. FIG. 5B depicts a graph 550 of voltage readings from a sensor system in accordance with an illustrative embodiment. In both comparisons 500 of FIG. 5A, a signal arm of a sensor system is compared to a reference arm of the sensor system. The signal arm refers to the cable of the sensor system exposed to an environment in an absorption channel. The reference arm refers to the reference cable of the sensor system that is isolated from the environment of the absorption channel. The light transmitted by both the signal arm and the reference arm is detected and measured by detection diodes, similar to the detection diodes described above with respect to FIG. 2. The measured intensity of the signal arm can be divided against that of the reference arm.

In the first comparison 510, the signal arm is exposed to an analyte, for example, carbon monoxide, while the reference arm is not exposed to the analyte. In the second comparison 520, no analyte is present in the absorption channel and thus the signal arm is exposed to a clean environment in the absorption channel. The reference arm is isolated from any environment of the absorption channel.

Figure 5B:
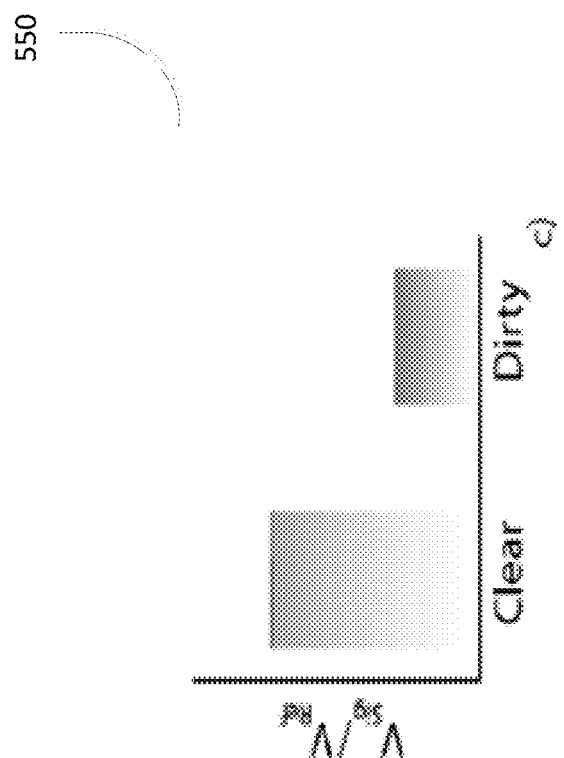
FIG. 5B depicts a graph of voltage readings from a sensor system in accordance with an illustrative embodiment.

As illustrated in FIG. 5B, a greater voltage is detected in the clean environment, corresponding to the second comparison 520 from FIG. 5A, as compared to the dirty environment, corresponding to the first comparison 510 from FIG. 5A. The lower voltage readings of the dirty environment are due to the presence of the analyte in the absorption channels, causing some of evanescent wave emitted by the signal arm to be absorbed by the analyte. In some embodiments, a calibration curve is used to determine the presence of an analyte. The calibration curve can be used to determine the presence of the analyte and the concentration of the analyte. In an embodiment, the calibration curve includes a set of standard samples of known concentrations. In other embodiments, the calibration curve includes threshold values for an environment of clean air.

Figure 6:
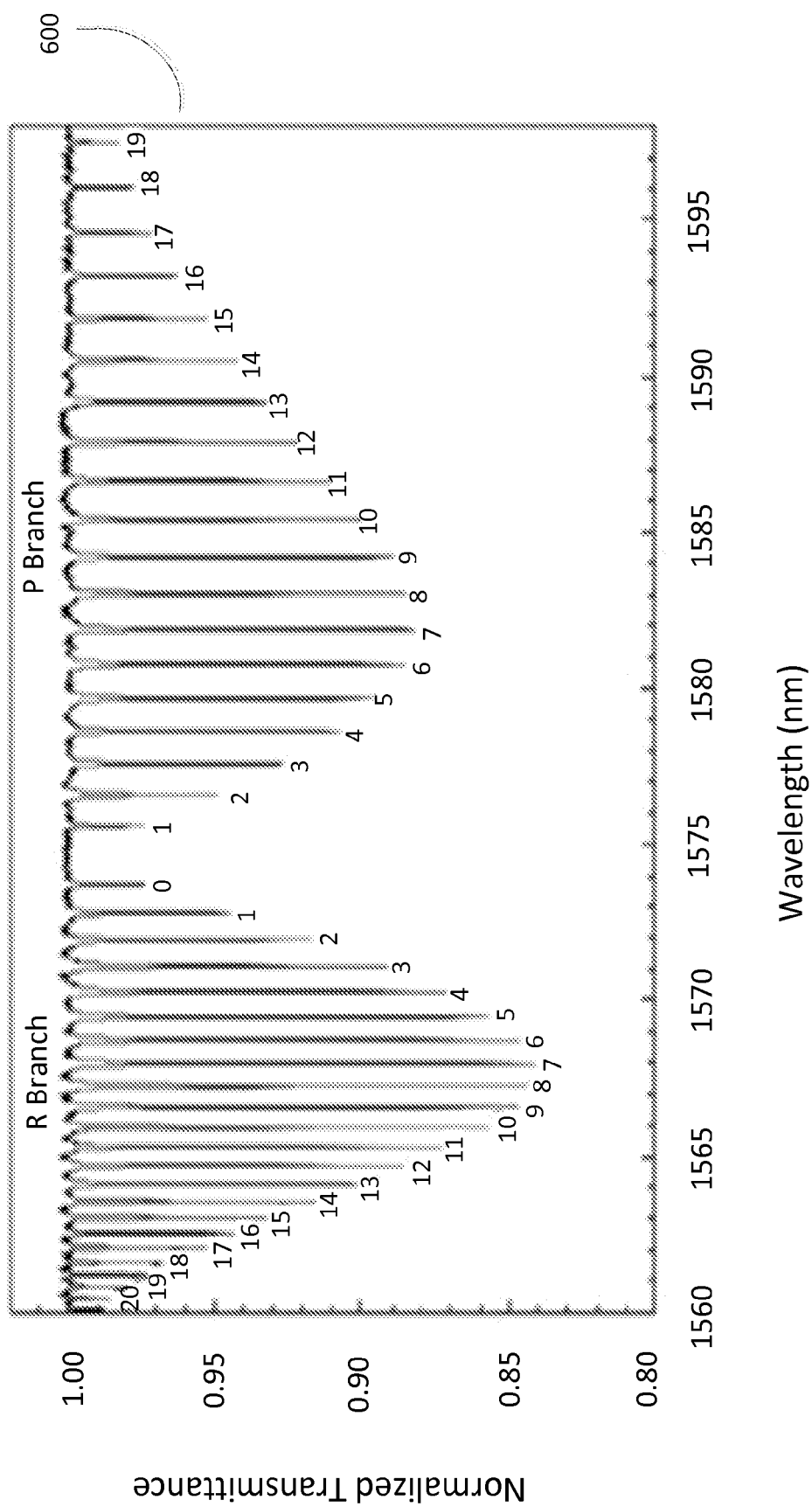
FIG. 6 depicts a graph of a carbon monoxide rotational-vibrational spectrum in accordance with an illustrative embodiment.

FIG. 6 depicts a graph 600 of a carbon monoxide rotational-vibrational spectrum. The graph shows the normalized transmittance power plotted as a function of wavelength of light. To protect against the possibility of environmental factors, for example, increased humidity or non-VOC detection resulting in false positive detections, the calibration curve can be used. In one embodiment, when an analyte is detected, the detected values can be compared to a calibration curve, similar to FIG. 6, to determine the type of analyte, as well as the concentration of the analyte.

In some embodiments, a detector of a sensor system communicates with a companion application on the mobile device. The companion application on the mobile device may host a calibration curve for the sensor system. In one embodiment, the calibration curve is programmed into the sensor system. In other embodiments, the calibration curve is programmed on a device in communication with the sensor system.

Figure 7:
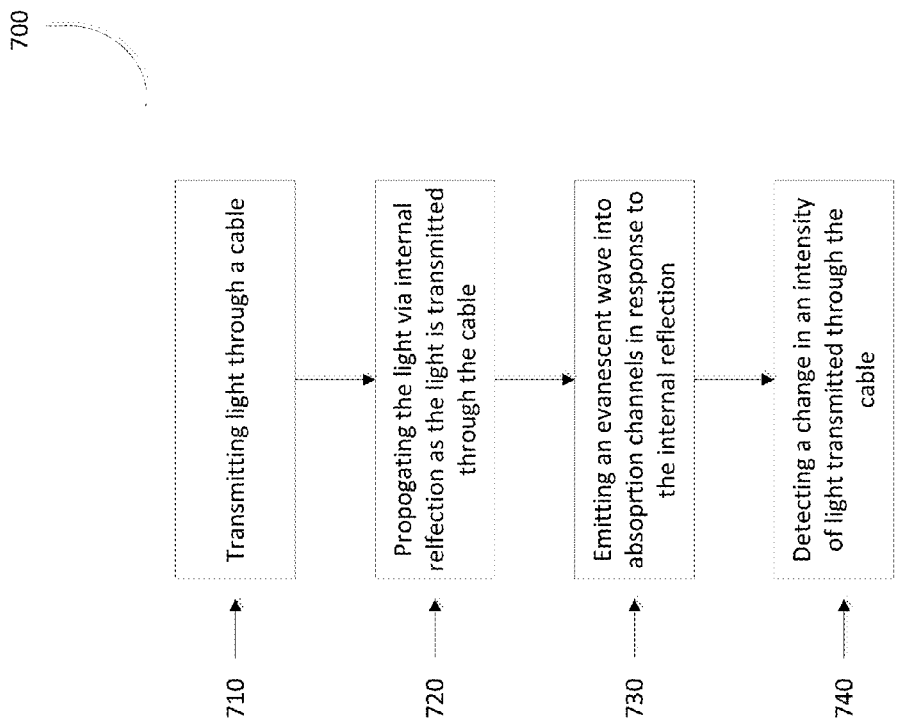
FIG. 7 depicts a flow diagram of a method for detecting analytes in an environment in accordance with an illustrative embodiment.

FIG. 7 depicts a flow diagram of a method 700 for detecting analytes in an environment in accordance with an illustrative embodiment. As a brief overview, the method 700 includes, transmitting, by a light source, light through a cable (operation 710). The method 700 further includes, propagating, by the cable, the light via internal reflection as the light is transmitted through the cable (operation 720). The method 700 further includes, emitting, by detection regions of the cable, an evanescent wave into absorption channels in response to the internal reflection (operation 730). The method 700 further includes detecting, by a detector, a change in an intensity of light transmitted through the cable (operation 740). The change in the intensity of light transmitted through the cable indicates the presence of an analyte in the absorption channels.

At operation 710, the method 700 includes transmitting, by a light source, light through a cable. The light source can transmit light to the detector through the cable. In an embodiment, an optical coupler is disposed between the light source and the detector. The light source transmits light to the optical coupler through the cable. The optical coupler splits or combines the light received from the light source and transmits the light to the detector. In an embodiment, the optical coupler can transmit the light received from the light source to the detector through both the cable and a reference cable.

At operation 720, the method 700 includes propagating, by the cable, the light via internal reflection as the light is transmitted through the cable and optionally the reference cable. At operation 730, the method 700 includes emitting, by detection regions of the cable, an evanescent wave into absorption channels in response to the internal reflection. In an embodiment, the detection regions are a portion of the cable exposed to an environment in the absorption channel. The evanescent wave is configured to excite a fluorophore or biological tag in total internal reflection fluorescence (TIRF) microscopy. The method includes chemically coating the absorption channels to attract a target analyte. In an embodiment, the absorption channels are chemically coated with a material to promote physisorption. In other embodiments, the absorption channels are chemically coated with a material to promote chemisorption. The chemical coating of the absorption channels creates a chemoselective environment in the absorption channel. The chemoselective environment can be created based on a desired analyte to be detected.

At operation 740, the method 700 includes detecting, by a detector, a change in an intensity of light transmitted through the cable. The change in the intensity of light transmitted through the cable indicates the presence of an analyte in the absorption channels. The change in the intensity of light transmitted through the cable corresponds to an amount of the evanescent wave that is absorbed by the analyte in the absorption channels. The analyte attracted to the environment of the absorption channel absorbs some of the evanescent wave emitted by the cable and reduces the intensity of the light received by the detector through the cable.

The detector detects a reduction in an intensity of the light transmitted through the cable. The detector is configured to detect the change in the intensity, P(x), of light transmitted through the cable, wherein P(x) is defined as:

$$P(x)=P_o e^{-\alpha r \mu L}$$

Wherein $P_o$ is a transmittance in an absence of absorbing gas (initial power), α is an absorption coefficient of gas in free space, r is a ratio of intensity of the evanescent wave to that of a propagating wave, L is a length of the detection region of the cable, and μ is a gas concentration. The detector compares the light detected from a reference cable to the light detected from the cable. The reference cable is isolated from the environment of the absorption channel and not affected by the presence of the analyte.

In an embodiment, the method 700 can further include transmitting, by the detector, the change in the intensity of light transmitted through the cable to a processor. The detector transmits the measured intensity of light transmitted by the reference cable to the processor. The processor can compare the change in the intensity of light transmitted through the cable to a calibration curve. In some embodiments, the calibration curve corresponds to threshold values for an environment with clean air, for example, an environment free of an analyte. The presence of an analyte in the absorption channel can indicate 'dirty' air in the environment around the sensor. The processor generates a notification in response to comparing the change in the intensity of light transmitted through the cable to the calibration curve. The processor can generate the notification to alert a user of a mobile device that the sensor is coupled with of the presence of the analyte in the environment around the device. The processor generates at least one of an auditory notification, a visual notification, a tactile notification, or a combination of them. For example, in one embodiment, the processor causes a mobile device to vibrate and the screen of the mobile device to flash in response to detecting the presence of the analyte.

Figure 8:
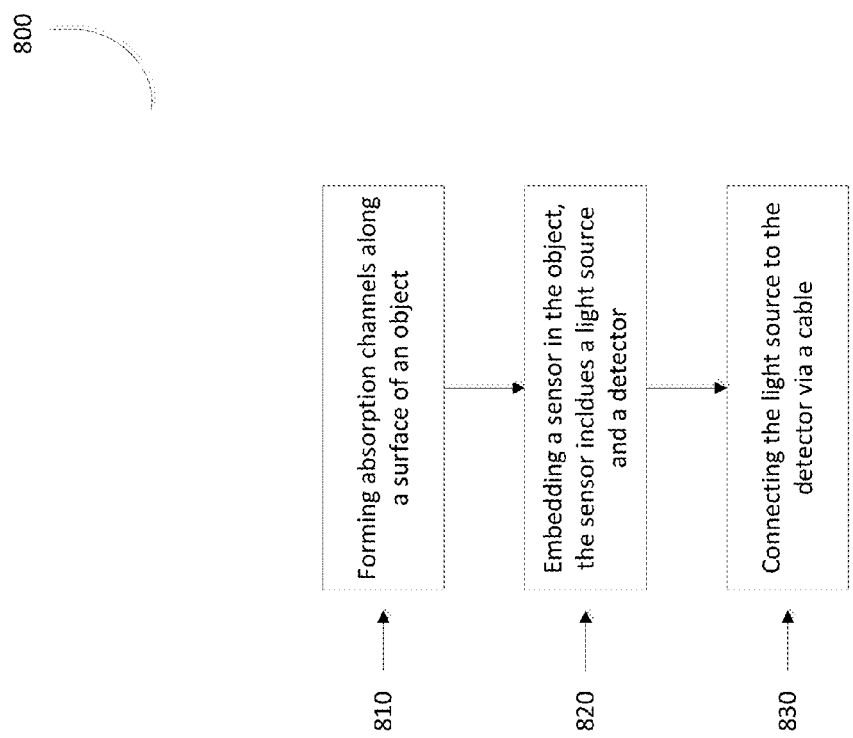
FIG. 8 depicts a flow diagram of a method for creating a sensor system for detecting analytes in accordance with an illustrative embodiment.

FIG. 8 depicts a flow diagram of a method for creating a sensor system in accordance with an illustrative embodiment. The method 800 includes forming absorption channels along a surface of an object (operation 810). The absorption channels can be configured to trap an analyte. To attract and/or trap the analyte, the absorption channels are chemically coated as discussed above. In various embodiments, at least one absorption channel may be chemically coated with a material to promote physisorption or chemisorption. In an embodiment, the sensor system includes multiple absorption channels and each of the absorption channels are chemically coated. In some embodiments, the absorption channels in a sensor system are all chemically coated with the same material. In other embodiments, the absorption channels in a sensor system are all chemically coated with a different material. In some embodiments, the object includes a mobile phone case and the method includes positioning the absorption channels along an outer surface of the mobile phone case.

The method 800 includes embedding a sensor in the object (operation 820). The sensor can be configured to detect the presence of the analyte. In an embodiment, the sensor includes a light source configured to transmit light and a detector configured to detect a change in an intensity of light transmitted by the light source.

The method 800 further includes connecting the light source to the detector via a cable (operation 830). The cable includes detection regions. The detection regions include a portion of the cable that is exposed to an environment within the absorption channel. In some embodiments, each of the detection regions are exposed in a different absorption channel. The method 800 can include disposing an optical coupler between the light source and the detector. In one embodiment, the optical coupler includes a 1:2 optical coupler. The 1:2 optical coupler can be configured to transfer light from the light source to the cable and a reference cable.

The method 800 includes connecting the light source to the detector via a reference cable. In an embodiment, the reference cable is protected from the absorption channels. The method 800 includes coupling a universal serial bus (USB) interface to the sensor. The USB interface connects the sensor to a computing device to power the sensor. The USB interface can be configured to transmit data between the sensor and the computing device.

In an embodiment, a processor is coupled to the sensor. The processor is configured to receive data from the sensor. The processor can receive the data through the USB interface of the sensor. In an embodiment, the data includes the intensity of light transmitted through the cable detected by the sensor. The processor compares the intensity of light transmitted through the cable detected by the embedded sensor to a calibration curve.

EXAMPLES

Example 1

Chemical Sensor Detects Carbon Monoxide

A mobile device has a mobile phone case with an embedded chemical sensor. The embedded chemical sensor is powered by the mobile device through a USB port and communicates with the mobile device through the USB port. The mobile phone case has three absorption channels formed into an upper surface. Each of the absorption channels is chemically coated with a different material. The first absorption channel is chemically coated with sulfur to attract carbon monoxide. The second absorption channel is coated with activated carbon to attract acetone. The third absorption channel is chemically coated with a zeolite to attract a larger VOC.

The embedded chemical sensor includes a bundle of optical fiber that connects an IR LED light source to a photodetector. The light transmitted by the IR LED light is split by a 1:2 optical coupler and transmitted to the photodetector. Connected to the 1:2 optical coupler to the photodetector is a signal arm and a reference arm of the bundle of optical fiber. The reference arm of the bundle of optical fiber transmits light to the detector. The reference arm is isolated from the absorption channels and completely encapsulated by the mobile phone case.

The signal arm of the bundle of optical fiber transmits the light to the detector. The signal arm includes detection regions that are exposed to the environment in the absorption channels. Each of the absorption channel includes holes in the surface of the absorption channels that allows the signal arm to directly interact with the environment in the absorption channels. Light propagates through the signal arm by total-internal reflection and an evanescent wave is emitted from the signal arm. The portions of the signal arm exposed to the absorption channels, the detection regions, emit the evanescent wave into the absorption channels.

An individual carries the mobile device into a construction area to test for chemicals and/or gases present. The construction area contains levels of carbon monoxide of which the individual is previously unaware. When the individual enters the construction area, the carbon monoxide in the air is attracted to the first absorption channel of the mobile phone case due to the coating of sulfur. The evanescent wave emitted by the detection regions of the signal arm interacts and is absorbed by the carbon monoxide molecules in the absorption channel. The absorption of the evanescent wave results in a change in the intensity of the light transmitted through the signal arm.

The photodetector detects the change in intensity of the signal arm by comparing the intensity of the light transmitted by the signal arm to the light transmitted by the reference arm. The photodetector includes two detection diodes, a signal detection diode and a reference detection diode. The signal detection diode is connected to the signal arm. The reference detection diode is connected to the reference arm. The photodetector compares the measurements taken by the signal detection diode to the measurements taken by the reference detection diode. The change in intensity between the signal arm and the reference arm indicates the presence of an analyte, carbon monoxide.

In response to detecting carbon monoxide, the chemical sensor communicates with a microprocessor of the mobile device. The chemical sensor instructs the mobile device to vibrate and flash a warning on a user interface of the mobile device to warn the individual of the presence of carbon monoxide.

Example 2

Chemical Sensor in a Clean Air Environment

A mobile device has a mobile phone case with an embedded chemical sensor. The embedded chemical sensor is powered by the mobile device through a USB port and communicates with the mobile device through the USB port. The mobile phone case has two absorption channels formed into an upper surface. Each of the absorption channels is chemically coated with the same material, sulfur, to attract carbon monoxide.

The embedded chemical sensor includes a bundle of optical fiber that connects an IR LED light source to a photodetector. The light transmitted by the IR LED light is split by a 1:2 optical coupler and transmitted to the photodetector. Connected to the 1:2 optical coupler to the photodetector is a signal arm and a reference arm of the bundle of fiber optic. The reference arm of the bundle of optical fiber transmits light to the detector. The reference arm is isolated from the absorption channels and completely encapsulated by the mobile phone case.

The signal arm of the bundle of optical fiber transmits the light to the detector. The signal arm includes detection regions that are exposed to the environment in the absorption channels. Each of the absorption channels includes holes in the surface of the absorption channels that allows the signal arm to directly interact with the environment in the absorption channels. Light propagates through the signal arm by total-internal reflection and an evanescent wave is emitted from the signal arm. The portions of the signal arm exposed to the absorption channels, the detection regions, emit the evanescent wave into the absorption channels.

An individual carries the mobile device into a construction area to test for chemicals and/or gases present. The construction area is outside in a humid environment; however, the air in the construction area is clean. When the individual enters the construction area, the humidity in the air interacts with each of the absorption channels of the mobile phone case. The evanescent wave emitted by the detection regions of the signal arm interacts with the humid air and is absorbed by the humid air in the absorption channel. The absorption of the evanescent wave results in a change in the intensity of the light transmitted through the signal arm.

The photodetector detects the change in intensity of the signal arm by comparing the intensity of the light transmitted by the signal arm to the light transmitted by the reference arm. The photodetector includes two detection diodes, a signal detection diode and a reference detection diode. The signal detection diode is connected to the signal arm. The reference detection diode is connected to the reference arm. The photodetector compares the measurements taken by the signal detection diode to the measurements taken by the reference detection diode. The change in intensity between the signal arm and the reference arm indicates the presence of an analyte, carbon monoxide. The photodetector transmits the data indicating the presence of carbon monoxide to a companion application on the mobile device. The companion application includes a calibration curve. The companion device compares the data received from the photodetector to the calibration curve. The comparison indicates that the change in intensity detected is due to a humid environment and not the presence of carbon monoxide.

In response to detecting the humid environment, the companion device communicates with a microprocessor of the mobile device. The companion device generates a notification to the user to indicate that the construction environment is clean.

Implementations of the subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, i.e., one or more circuits of computer program instructions, encoded on one or more computer storage media for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices).

The term "data processing apparatus" or "computing device" encompasses various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a circuit, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more circuits, sub programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations,"

without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A system for detecting an analyte, the system comprising:
   an absorption channel positioned along a surface of an object, wherein the absorption channel is configured to trap the analyte, and wherein the absorption channel includes a wall having one or more holes therein;
   a sensor embedded in the object and configured to detect the presence of the analyte, the sensor comprising:
   a light source configured to transmit light;
   a detector configured to detect a change in an intensity of the light transmitted by the light source; and
   a cable configured to connect the light source to the detector, wherein the cable comprises a cladding layer and detection regions, and wherein the detection regions comprise a portion of the cable exposed to the analyte in the absorption channel through the one or more holes within the wall of the absorption channel; and
   an index matching material disposed along the wall of the absorption channel, wherein the index matching material has an index of refraction that substantially matches an index of refraction of the cladding layer of the cable.

2. The system of claim 1, wherein the absorption channel is chemically coated with a material to attract the analyte, and wherein the material is selected to promote at least one of physisorption or chemisorption.

3. The system of claim 2, wherein the material is at least one of sulfur, aluminum-doped graphene, activated carbon, or a zeolite mineral.

4. The system of claim 1, wherein the analyte is at least one of carbon monoxide, acetone, or cyclohexane.

5. The system of claim 1, wherein the object comprises a mobile phone case, and wherein the absorption channel is positioned along an outer surface of the mobile phone case.

6. The system of claim 1, wherein the sensor further comprises a 1:2 optical coupler disposed between the light source and the detector, and wherein the 1:2 optical coupler is configured to transfer light from the light source to the cable and a reference cable.

7. The system of claim 1, wherein the sensor further comprises a reference cable, and wherein the reference cable connects the light source to the detector and is protected from the absorption channel.

8. The system of claim 1, further comprising a plurality of absorption channels, wherein each of the detection regions is exposed in a different absorption channel.

9. The system of claim 1, further comprising a processor coupled to the sensor, wherein the processor is configured to:
   receive data from the sensor, wherein the data comprises the intensity of light transmitted through the cable detected by the sensor; and
   compare the intensity of light transmitted through the cable detected by the sensor to a calibration curve.

10. A method of preparing a chemical sensor, the method comprising:
    forming an absorption channel along a surface of an object, wherein the absorption channel is configured to trap an analyte, and wherein the absorption channel includes a wall having one or more holes therein;
    embedding a sensor in the object, wherein the sensor is configured to detect the presence of the analyte, the sensor comprising:
    a light source configured to transmit light;
    a detector configured to detect a change in an intensity of the light transmitted by the light source; and
    connecting the light source to the detector via a cable, wherein the cable comprises a cladding layer and detection regions, and wherein the detection regions comprise a portion of the cable exposed to the analyte in the absorption channel through the one or more holes within the wall of the absorption channel; and
    forming an index matching material along the wall of the absorption channel, wherein the index matching material has an index of refraction that substantially matches an index of refraction of the cladding layer of the cable.

11. The method of claim 10, further comprising chemically coating the absorption channel with a material, wherein the material is selected to promote at least one of physisorption or chemisorption.

12. The method of claim 10, further comprising disposing a 1:2 optical coupler between the light source and the detector, wherein the 1:2 optical coupler is configured to transfer light from the light source to the cable and a reference cable.

13. The method of claim 10, further comprising connecting the light source to the detector via a reference cable, wherein the reference cable is protected from the absorption channel.

14. The method of claim 10, further comprising forming a plurality of absorption channels, wherein each of the detection regions is exposed in a different absorption channel.

15. The method of claim 10, further comprising coupling a processor to the sensor, wherein the processor is configured to:
    receive data from the sensor, wherein the data comprises the intensity of light transmitted through the cable detected by the sensor; and
    compare the intensity of light transmitted through the cable detected by the sensor to a calibration curve.

16. The system of claim 1, wherein the one or more holes extend between the wall of the absorption channel and the cable.

17. The system of claim 1, wherein the one or more holes extend an entire length of the absorption channel.

18. The system of claim 17, wherein the cable extends along the entire length of the absorption channel.

19. The system of claim 1, further comprising a plurality of absorption channels, and wherein the cable extends along an entire length of each of the plurality of absorption channels.

20. The system of claim 19, wherein each absorption channel of the plurality of absorption channels is spaced apart from other absorption channels.

* * * * *

UNITED STATES PATENT AND TRADEMARK OFFICE
CERTIFICATE OF CORRECTION

| | |
|---|---|
| PATENT NO. | : 9,680,271 B2 |
| APPLICATION NO. | : 14/492748 |
| DATED | : June 13, 2017 |
| INVENTOR(S) | : Saari et al. |

Page 1 of 1

It is certified that error appears in the above-identified patent and that said Letters Patent is hereby corrected as shown below:

In the Specification

In Column 5, Line 33, delete "object 220" and insert -- object 205 --, therefor.

In Column 5, Line 33, delete "light source 205" and insert -- light source 220 --, therefor.

In Column 16, Line 49, delete "recitation no" and insert -- recitation, no --, therefor.

In Column 17, Line 4, delete "general such" and insert -- general, such --, therefor.

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*